(12) United States Patent
Salzillo et al.

(10) Patent No.: US 9,588,075 B2
(45) Date of Patent: Mar. 7, 2017

(54) SENSOR FOR DETECTING HYDROGEN IONS IN AN AQUEOUS SOLUTION

(71) Applicant: STMicroelectronics S.r.l., Agrate Brianza (IT)

(72) Inventors: Giovanna Salzillo, Teverola (IT); Rossana Scaldaferri, Sapri (IT); Valeria Casuscelli, Naples (IT); Luigi Giuseppe Occhipinti, Ragusa (IT)

(73) Assignee: STMICROELECTRONICS S.R.L., Agrate Brianza (IT)

( * ) Notice: Subject to any disclaimer, the term of this patent is extended or adjusted under 35 U.S.C. 154(b) by 360 days.

(21) Appl. No.: 14/200,576

(22) Filed: Mar. 7, 2014

(65) Prior Publication Data
US 2014/0251805 A1    Sep. 11, 2014

(30) Foreign Application Priority Data

Mar. 8, 2013   (IT) ............... MI2013A0355

(51) Int. Cl.
| | | |
|---|---|---|
| C25D 17/00 | (2006.01) | |
| G01N 27/30 | (2006.01) | |
| G01N 27/333 | (2006.01) | |
| G01N 27/416 | (2006.01) | |

(52) U.S. Cl.
CPC ....... *G01N 27/302* (2013.01); *G01N 27/3335* (2013.01); *G01N 27/4167* (2013.01)

(58) Field of Classification Search
CPC .......... G01N 27/4071; G01N 27/3335; G01N 27/4167
USPC ....................................... 204/406
See application file for complete search history.

(56) References Cited

U.S. PATENT DOCUMENTS

2005/0109637 A1* 5/2005 Iyengar .............. A61B 5/14532
205/775

OTHER PUBLICATIONS

Maattanen, A. (2013). "A low-cost paper-based inkjet-printed platform for electrochemical analyses." Sensors and Actuators B. 177:153-162.*
Tongol, B.J.V. (2003). "Surface and electrochemical studies of a carbon dioxide probe based on conducting polypyrrole." Sensors and Actuators B. 93:187-196.*
Du, X. and Wang, Z., "Effects of polymerization potential on the properties of electrosynthesized PEDOT films," Electrochimica Acta (48):1713-1717, 2003.
Maattanen, A., et al., "A low-cost paper-based inkjet-printed platform for electrochemical analyses," Sensors and Actuators B (177), pp. 153-162, 2013.
Thompson, B. C. et al., "A Solid-State pH Sensor for Nonaqueous Media Including Ionic Liquids," Anal. Chem. (85):3521-3525, 2013.

(Continued)

*Primary Examiner* — Jyoti Nagpaul
(74) *Attorney, Agent, or Firm* — Seed IP Law Group LLP

(57) ABSTRACT

The present disclosure relates to a sensor for detecting hydrogen ions in an aqueous solution comprising a support, a reference electrode, a working electrode and a counter electrode supported by said support, the reference electrode being made of a material comprising silver and silver chloride, the counter electrode being made of a conductive material. The working electrode comprises a substrate and a layer made of an inherently electrically conductive polymer of the polythiophene or polyaniline (PANI) or polypyrrole class.

16 Claims, 4 Drawing Sheets

(56) References Cited

OTHER PUBLICATIONS

Tongol, B. J. V. et al., "Surface and electrochemical studies of a carbon dioxide probe based on conducting polypyrrole," Sensors and Actuators B(93):187-196, 2003.

Yuqing, M. et al., "New technology for the detection of pH," J. Biochem. Biophys. Methods (63):1-9, 2005.

* cited by examiner

SENSOR FOR DETECTING HYDROGEN IONS IN AN AQUEOUS SOLUTION

BACKGROUND

Technical Field

The present disclosure relates to a sensor for detecting hydrogen ions in an aqueous solution, e.g., the pH or $CO_2$ level and to an apparatus for detecting hydrogen ions in an aqueous solution using said sensor.

Description of the Related Art

The concentration of hydrogen ions, i.e., the pH or $CO_2$ in a solution and more generally in a liquid product, is a very important measurement made in many research activities and industrial manufacturing processes.

For instance, the pH is typically measured in the food and beverage industry, as well as in body care products, in pharmaceuticals, in water and waste product treatment.

Many sensors exist in the art for detecting the pH value of a liquid product, either for laboratory research or industrial detection purposes.

The paper "New Technology for the Detection of pH", in "Journal of Biochemical and Biophysical Methods", by Miao Yuquing et al., Elsevier B. V., 2005, describes a variety of pH sensors and provides indications about the physical operation principles of such sensors.

One of these prior art sensors, which is extensively used for pH measurement, uses glass electrodes. Prior art glass electrode-based pH sensors use a potentiometric detection method and include a measuring glass electrode and a separate reference electrode in a buffer solution containing a conductive potassium chloride (KCl) gel.

These electrodes are usually accommodated in a combined electrode containing both electrodes, which is connected to an electronic meter having a signal amplifier and temperature compensation. A silver wire enclosed in the measuring electrode allows the passage of a signal indicating the difference between the pH values of the solutions inside and outside the glass membrane.

The reference electrode has a fixed and stable potential, which is independent of the solution being measured and is calibrated outside the system in a reference solution.

The most commonly used reference electrode is a silver— silver chloride electrode placed in a saturated saline or in gel.

The measuring and reference electrodes form a circuit that allows measurement of the voltage generated by the glass electrode.

While glass electrodes allow their sensors to operate and detect pH values over the entire scale of values from 0 to 14, they still suffer from the drawback that, for detection accuracy, they must be carried in a buffer solution and maintained in a wet state.

Further potential drawbacks of pH glass electrodes include physical fragility, leakage of the reference electrode solution into the sample solution to be measured, poor response in low ionic strength solutions, high background noise and low signal-to-noise ratio.

Other known types of pH sensors are those named ISFET (ion-sensitive field effect transistors) which are used in applications for which glass electrodes are inadequate.

Namely, these transistor sensors are sensitive to hydrogen ion concentration, and their sensitive part relies on an electroactive gate that restricts electric current flow as a function of hydrogen ion concentration.

Changes in ion concentration alter the current flowing through the transistor. The most commonly used materials for pH sensitive gates include silicon dioxide ($SiO_2$) and tantalum pentaoxide ($Ta_2O_5$).

Since ISFET sensors provide quick measurements and are less temperature-dependent than glass electrodes, they afford longer maintenance and calibration intervals, and further provide the advantage of allowing miniaturization and automation.

Nevertheless, due to a lack of linearity at the ends of the pH spectrum, they have the drawback of providing a restricted pH analysis interval, from 2 to 12.

Concerning optical sensors, they use a photodetector to measure fluorescence changes in a fluorine-based indicator, as a function of the pH.

Many fluorine-based indicators or dyes are available, which change fluorescence with $H_3O+$ concentration.

These sensors do not require calibration but have drawbacks including irregularity, photo bleaching (which means that the optical sensors must be kept in the dark to retain their effectiveness), leaching of the pH sensitive chromophore into the sample solution beyond restricted pH ranges.

Referring now to sensors that use electrodes comprising electrically conductive polymers, generally designated as CPs, those that are known in the art use platinum electrodes with a conductive polymer comprising poly(m-phenylene-diamine) or generally an anyline-, thiophene- or benzene-derivative based polymer deposited thereon, particularly by electropolymerization.

While these pH sensors have the advantage that they may be formed as an entirely solid-state device, and are substantially temperature independent, those that are currently known and tested have a relatively slow response, and do not allow effective reuse for testing different products or solutions.

BRIEF SUMMARY

One embodiment of the present disclosure is a sensor for detecting hydrogen ions in an aqueous solution (or liquid products), that obviates the drawbacks of prior art sensors, particularly those as mentioned above, and is reusable in any liquid product to be tested.

One embodiment is sensor for detecting hydrogen ions in an aqueous solution and includes a support; a reference electrode made of a material that includes silver and silver chloride and supported by the support; a conductive counter electrode supported by said support; and a working electrode supported by the support and including a substrate and a layer made of an inherently electrically conductive polymer of the polythiophene or polyaniline (PANI) or polypyrrole class.

BRIEF DESCRIPTION OF THE SEVERAL VIEWS OF THE DRAWINGS

The disclosure will be now described in greater detail with reference to a few embodiments, which are shown by way of illustration and without limitation in the accompanying drawings, in which.

DETAILED DESCRIPTION

Even when this is not expressly stated, the individual features as described with reference to the particular embodiments shall be intended as auxiliary to and/or interchangeable with other features described with reference to other exemplary embodiments.

Figure 1:
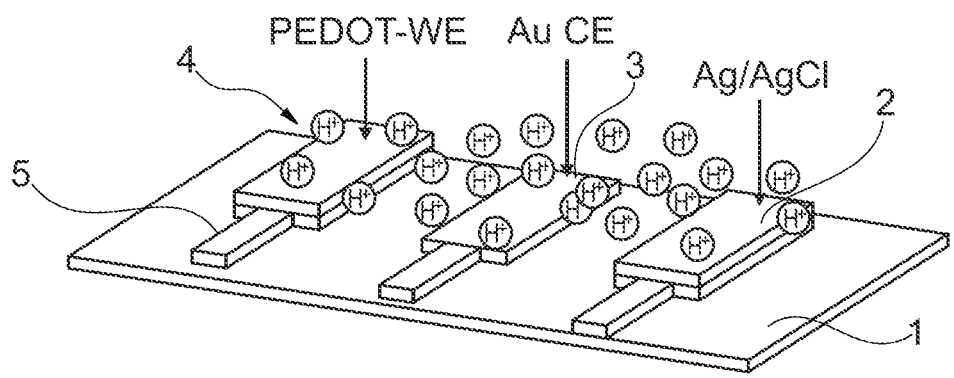
FIG. 1 is a schematic perspective view of an embodiment of a pH sensor of the present disclosure.
Figure 2:
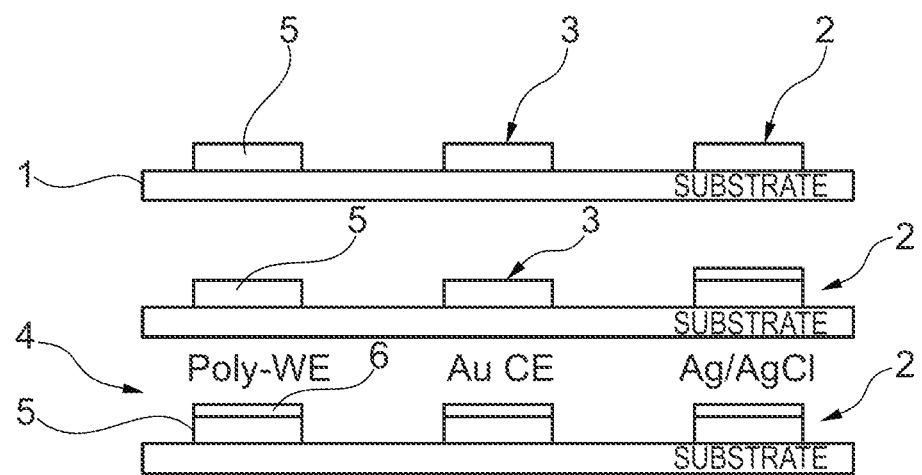
FIG. 2 schematically shows the method of making the sensor of FIG. 1.

Referring to the above mentioned figures and particularly to FIGS. 1 and 2, a sensor of the disclosure for detecting the pH level of a liquid product comprises a base support 1. This base support 1 has a reference electrode (RE) 2, a counter electrode (CE) 3 and a working electrode (WE) 4 mounted thereto.

In accordance with the embodiment as schematically shown in FIGS. 1 and 2, the base support 1 is formed as a platform and the electrodes 2, 3 and 4 are coplanarly arranged on said platform.

The reference electrode 2 is preferably made from a material comprising silver and silver chloride (Ag/AgCl), whereas the counter electrode 3 is made from a material comprising gold (Au).

The working electrode 5 comprises a substrate 5 and a film 6 made of an inherently electrically conductive polymer of the polythiophene class.

In an alternative embodiment of the working electrode 4, the conductive polymers for making such electrode may also include polyaniline (PANI) or polypyrrole. The substrate 5 of the electrode 4 comprises a conductive material that preferably includes gold (Au) or indium-tin oxide (ITO).

The film 6 of a preferred embodiment of the disclosure is made of poly(3,4-ethylenedioxythiophene) (PEDOT).

The film 6 made of such inherently electrically conductive polymer (PEDOT) is preferably formed by direct electropolymerization on the substrate 5 from the EDOT monomer, e.g., in a process as described in the paper "Effects of Polymerization Potential on Properties of Electrosynthesized PEDOT films" by X. Du et al., ELETTROCHIMICA ACTA NO 48, 2003.

Particularly, the film 6 is obtained by 5 voltage application cycles, with voltages ranging from 0.5 V to 1.5 V, using a scan rate of 40 mV/sec, at room temperature.

FIG. 2 shows the subsequent steps, in which the working electrode 4 of the sensor is formed, from placement of the substrate 5 on the support 1 to deposition of the PEDOT polymer, and formation of the film 6.

Figure 3:
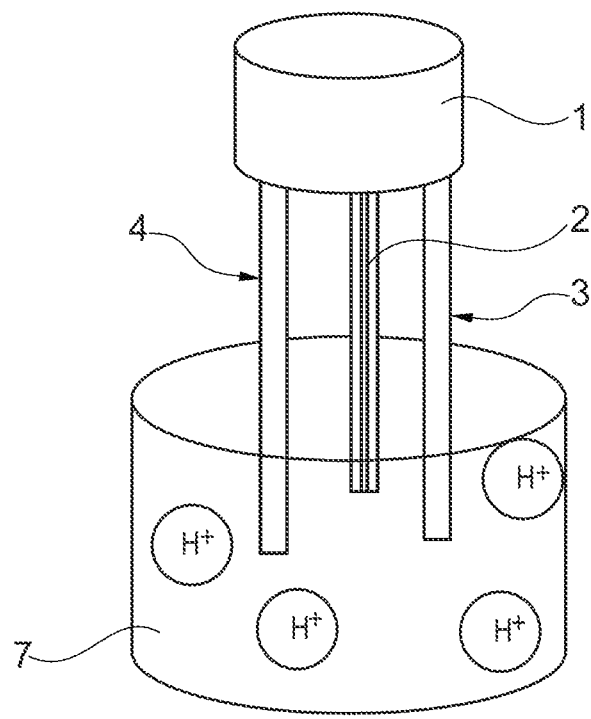
FIG. 3 shows a sectional perspective view of an alternative embodiment of the sensor of the disclosure.
Figure 4:
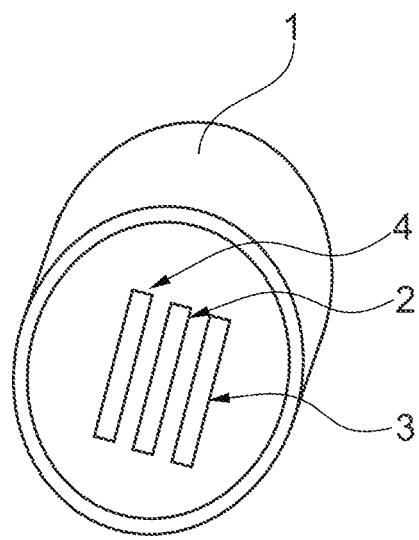
FIG. 4 is a bottom perspective view of the sensor of FIG. 3.

Referring to FIGS. 3 and 4, in a different embodiment of the disclosure, the reference electrode (RE) 2, the counter electrode (CE) 3 and the working electrode (WE) 4 are at angles to a direction perpendicular to the plane that contains the platform-shaped support 1.

Particularly, these electrodes 2, 3 and 4 are arranged perpendicular to the plane that contains said platform-shaped support 1.

Also in the embodiment of FIGS. 3 and 4, the working electrode (WE) 4 comprises a PEDOT film which is directly polymerized on the substrate of the electrode, using the methods as mentioned above concerning the embodiment of FIGS. 1 and 2.

In order to test pH sensitivity, a sensor formed according to the present disclosure was introduced into an amperometric measurement circuit, which is known to measure the current intensity caused by an oxidation-reduction reaction (redox). Current intensity is directly proportional to the concentration of the active species derived by the redox, in the solution being tested, e.g., hydrogen ions $H+$ whose concentration represents the pH. Therefore, for a given bias voltage applied to the circuit, resistance values may be determined, representing a corresponding pH value.

A sensor of the disclosure was tested with a number of solutions, whose pH ranged from 2 to 12.

These solutions were prepared using a mixture of sodium phosphate, biphasic sodium phosphate, sodium dihydrogen phosphate and phosphoric acid, and each mixture was placed in a respective cell as the one schematically referenced 7 in FIG. 3. The device was characterized by means of cyclic voltage measurements from −0.15 V to 0.15 V and from 0.15 V to −0.15V with a scan rate of 40 mV/sec, repeated for two cycles. The comparison between the measured voltages and the corresponding pH values showed that current intensity through the cell containing the solution decreased as pH increased.

Extraction of resistance values at a fixed voltage of −0.10 V showed a linear increase of resistances with the pH values.

Figure 5:
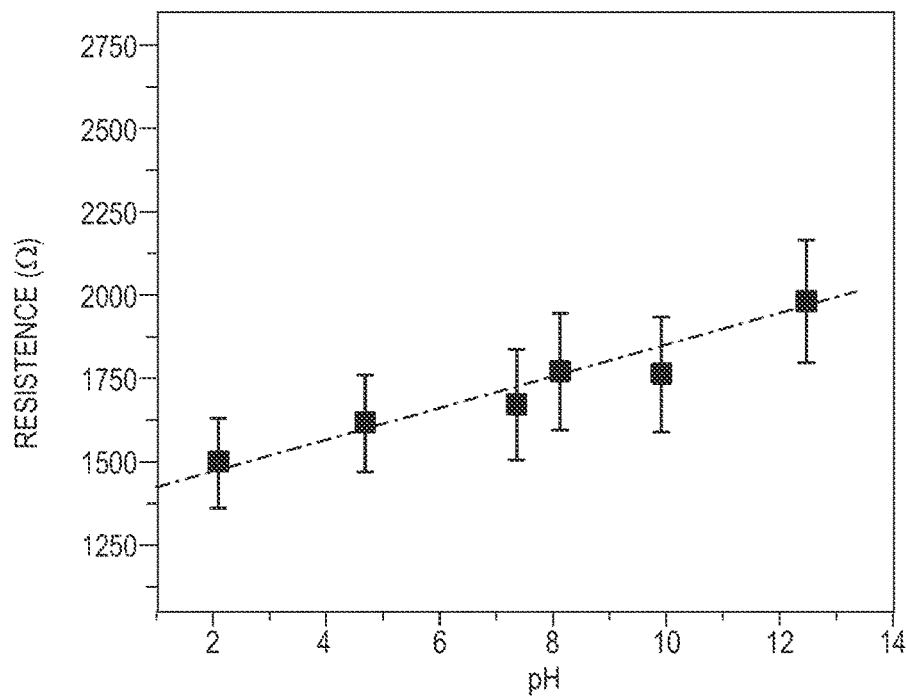
FIG. 5 is a diagram that shows the correlation between the pH value and the resistance value as measured using an amperometric apparatus connected to the working electrode (WE) of a sensor of the disclosure, which is reused for pH detection in different solutions.
Figure 6:
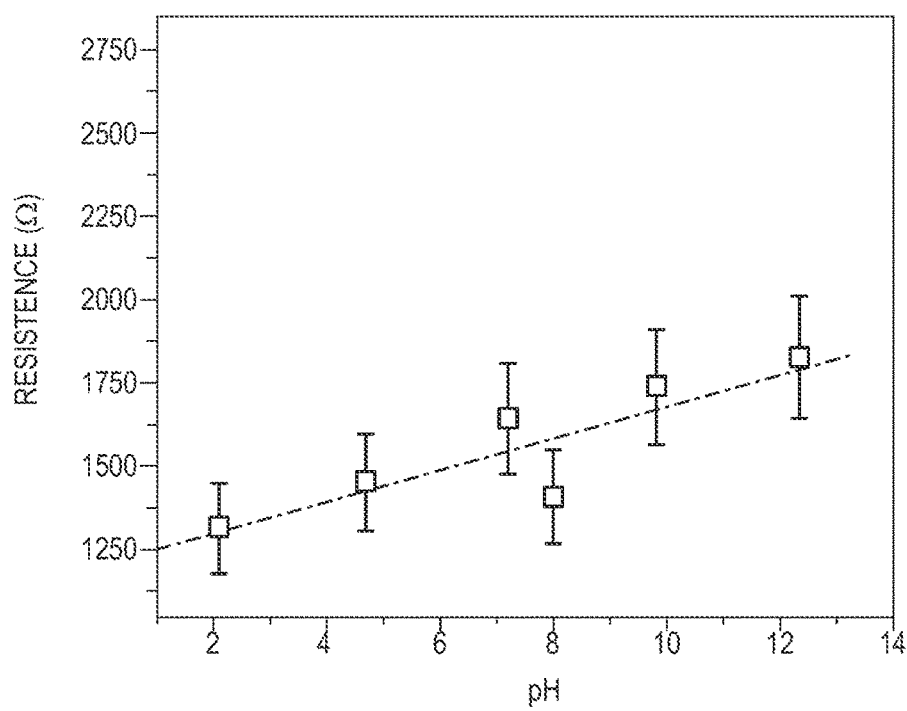
FIG. 6 is a diagram that shows the correlation between the pH value and the resistance value as measured using an amperometric apparatus connected to the working electrode (WE) of several sensors of the disclosure, which are used for pH detection in respective different solutions.

The data obtained therefrom, considering possible testing errors, is represented in the diagrams of FIGS. 5 and 6 and shows that resistance values increase with pH according to a linear equation with a correlation coefficient $R=0.97$, in the range of tested values, from 2 to 12.

The diagram of FIG. 5 shows the curve of resistance as a function of the pH as detected using a single sensor that is reused for each of the solutions having a different pH, by simply rinsing it between measurements, whereas the diagram of FIG. 6 shows the curve of resistance as a function of pH as detected using a new sensor for each solution being analyzed.

Figure 7:
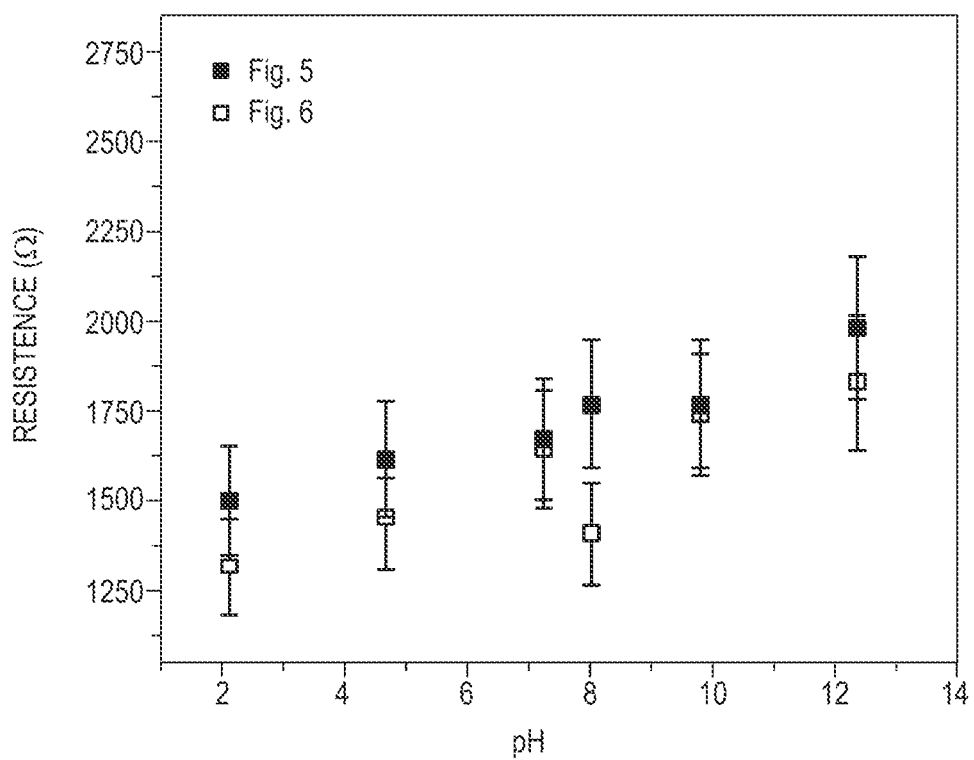
FIG. 7 shows the comparison of the diagrams of the previous FIGS. 5 and 6.

The comparison of the two diagrams, as shown in FIG. 7, shows that simple rinsing ensures adequate recovery of the functions of the sensor, and hence reliability of the results obtained thereby, which proves that the sensor of the disclosure provides an important operating advantage.

The sensor of the disclosure, introduced into the solution being analyzed, was found to have a response time of about 0.25 sec, and a sensitivity, given by the inclination of the resistance curve as a function of the pH value, of about 44 ohm/pH unit.

It shall be noted that the use of the pH sensor as described above may be also extended to a $CO_2$ sensor, due to the direct relation between the concentration of $CO_2$ and the concentration of $H+$ ions, i.e., the pH. Such a $CO_2$ sensor may be formed by introducing an electrolytic solution and a $CO_2$ gas-selective membrane in the device that was used as a pH sensor.

Therefore, the disclosure allows low-cost manufacture of apparatus for detection and measurement of hydrogen ions in an aqueous solution or a liquid product in general, which are entirely solid-state, sturdy apparatus, having a high sensitivity and requiring no particular preservation arrangement between successive uses, as they are unaffected by light and moisture.

Those skilled in the art will obviously appreciate that a number of changes and variants may be made to the above without departure from the scope of the present disclosure.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A sensor for detecting hydrogen ions in an aqueous solution comprising:
    a support;
    a reference electrode made of a material that includes silver and silver chloride and supported by the support;
    a conductive counter electrode supported by said support; and,
    a working electrode supported by the support and including a substrate and a layer made of an inherently electrically conductive polymer of the group consisting of polythiophene, polyaniline (PANT), and polypyrrole,
    wherein the sensor is a solid-state pH sensor.

2. The sensor as claimed in claim 1, wherein said inherently electrically conductive polymer is poly(3,4-ethylenedioxythiophene) (PEDOT).

3. The sensor as claimed in claim 2, wherein said layer made of said polymer (PEDOT) directly contacts said substrate.

4. The sensor as claimed in claim 1, wherein said substrate of the working electrode is made of a conductive material comprising gold (Au) or indium-tin oxide (ITO).

5. The sensor as claimed in claim 1, wherein said support is formed as a platform, and said reference electrode, said working electrode and said counter electrode are coplanarly arranged on said platform.

6. The sensor as claimed in claim 1, wherein said support is formed as a platform, and said reference electrode, said working electrode and said counter electrode extend at angles from a face of said platform.

7. The sensor as claimed in claim 6, wherein said electrodes are arranged perpendicular to the face of said platform.

8. The sensor as claimed in claim 1, comprising an electrolytic solution and a $CO_2$ gas-selective membrane coupled to the support.

9. An apparatus for detecting hydrogen ions in an aqueous solution comprising:
    a solid state pH sensor that includes:
        a support;
        a reference electrode made of a material that includes silver and silver chloride and supported by the support;
        a conductive counter electrode supported by said support; and,
        a working electrode supported by the support and including a substrate and a layer made of an inherently electrically conductive polymer of the group consisting of polythiophene, polyaniline (PAM), and polypyrrole;
    a measuring circuit that includes a voltage source configured to apply a voltage between said working electrode and said counter electrode; and
    an amperometric device configured to measure current flowing in said measuring circuit.

10. The apparatus as claimed in claim 9, wherein said amperometric device comprises a current-to-resistance converter.

11. The apparatus as claimed in claim 9, wherein said inherently electrically conductive polymer is poly(3,4-ethylenedioxythiophene) (PEDOT).

12. The apparatus as claimed in claim 11, wherein said layer made of said polymer (PEDOT) directly contacts said substrate.

13. The apparatus as claimed in claim 9, wherein said substrate of the working electrode is made of a conductive material comprising gold (Au) or indium-tin oxide (ITO).

14. The apparatus as claimed in claim 9, wherein said support is formed as a platform, and said reference electrode, said working electrode and said counter electrode are coplanarly arranged on said platform.

15. The apparatus as claimed in claim 9, wherein said support is formed as a platform, and said reference electrode, said working electrode and said counter electrode extend at angles from a face of said platform.

16. The apparatus as claimed in claim 15, wherein said electrodes are arranged perpendicular to the face of said platform.

* * * * *

UNITED STATES PATENT AND TRADEMARK OFFICE
CERTIFICATE OF CORRECTION

PATENT NO. : 9,588,075 B2
APPLICATION NO. : 14/200576
DATED : March 7, 2017
INVENTOR(S) : Giovanna Salzillo et al.

It is certified that error appears in the above-identified patent and that said Letters Patent is hereby corrected as shown below:

In the Claims

Column 6, Lines 19-20:
"consisting of polythiophene, polyaniline (PAM), and polypyrrole;" should read, --consisting of polythiophene, polyaniline (PANI), and polypyrrole;--.

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*